(12) United States Patent
Deisinger et al.

(10) Patent No.: US 8,687,178 B2
(45) Date of Patent: Apr. 1, 2014

(54) PROCESS FOR TESTING A LASER DEVICE

(75) Inventors: Thomas Deisinger, Zirndorf (DE); Christof Donitzky, Eckental/Eschenau (DE); Claudia Gorschboth, Nürnberg (DE); Richard Heimisch, Fürth (DE); Olaf Kittelmann, Berlin (DE); Gerhard Robl, Stein (DE); Martin Starigk, Nürnberg (DE); Klaus Vogler, Eschenau (DE); Mathias Wölfel, Erlangen (DE)

(73) Assignee: Wavelight GmbH, Erlangen (DE)

( * ) Notice: Subject to any disclaimer, the term of this patent is extended or adjusted under 35 U.S.C. 154(b) by 204 days.

(21) Appl. No.: 12/894,299

(22) Filed: Sep. 30, 2010

(65) Prior Publication Data

US 2012/0080586 A1   Apr. 5, 2012

(51) Int. Cl.
*G01J 1/00* (2006.01)
*G01J 1/42* (2006.01)
*A61F 9/008* (2006.01)

(52) U.S. Cl.
CPC ..... *G01J 1/4257* (2013.01); *A61F 2009/00855* (2013.01)
USPC .......................................................... 356/123

(58) Field of Classification Search
CPC ..................... G01J 1/4257; A61F 2009/00855
USPC ................ 356/121–127, 243.1, 243.5, 243.8; 250/252.1; 606/5, 10, 13
See application file for complete search history.

(56) References Cited

U.S. PATENT DOCUMENTS

| | | | |
|---|---|---|---|
| 4,638,502 A * | 1/1987 | Yaffe | 378/207 |
| 4,713,537 A * | 12/1987 | Kunz et al. | 250/252.1 |
| 4,762,495 A * | 8/1988 | Maloney et al. | 434/271 |
| 4,767,333 A * | 8/1988 | Born | 434/262 |
| 6,992,765 B2 | 1/2006 | Horvath et al. | |
| 7,474,393 B2 * | 1/2009 | Wojciechowski | 356/213 |
| 2004/0070761 A1 | 4/2004 | Horvath et al. | |
| 2006/0114469 A1 | 6/2006 | Horvath et al. | |
| 2008/0078751 A1 * | 4/2008 | Abrott | 219/121.69 |
| 2008/0214936 A1 * | 9/2008 | Wieringa et al. | 600/443 |
| 2009/0127429 A1 * | 5/2009 | Kittelmann et al. | 250/201.2 |
| 2009/0137988 A1 * | 5/2009 | Kurtz | 606/4 |
| 2009/0149841 A1 * | 6/2009 | Kurtz | 606/4 |
| 2009/0171327 A1 * | 7/2009 | Kurtz et al. | 606/6 |
| 2010/0228236 A1 | 9/2010 | Muhlhoff et al. | |

FOREIGN PATENT DOCUMENTS

| | | |
|---|---|---|
| DE | 102007056554 A1 | 5/2009 |
| WO | 2008/040436 A1 | 4/2008 |
| WO | 2009/059251 A2 | 5/2009 |

* cited by examiner

*Primary Examiner* — Gregory J Toatley
*Assistant Examiner* — Rufus Phillips

(57) ABSTRACT

A process is proposed for testing a laser device that has been set up to emit pulsed focused laser radiation, the focal position of which is adjustable both in and across the direction of propagation of the laser radiation. The laser device includes a contact element that is transparent to the laser radiation, with an abutment surface for abutment of an object to be machined. Within the scope of the process, a test object that is transparent to the laser radiation at least in a machining region is applied onto the abutment surface of the contact element. Then laser radiation is beamed into the test object bearing against the abutment surface and in the process the focal position is moved in accordance with a predetermined test pattern, in order to generate enduring machining structures in the test object.

16 Claims, 4 Drawing Sheets

Fig. 1
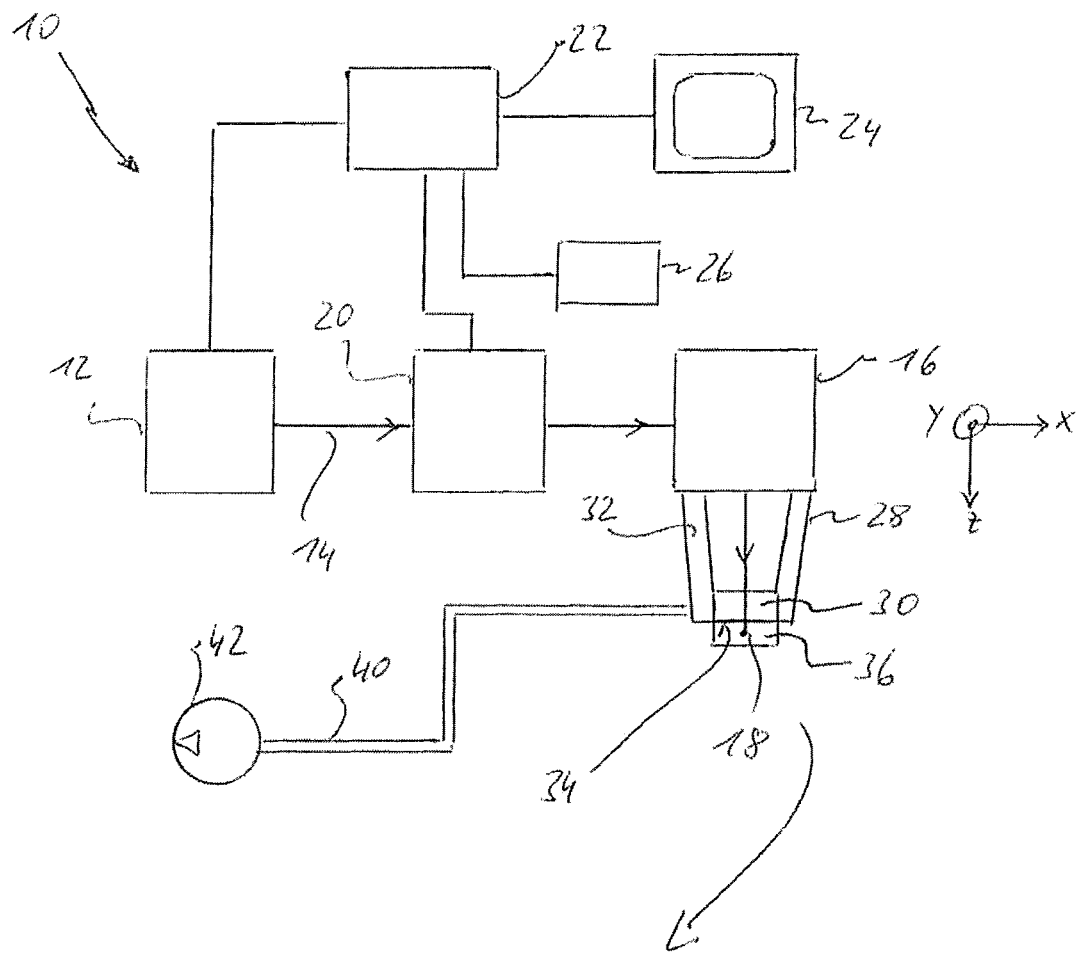
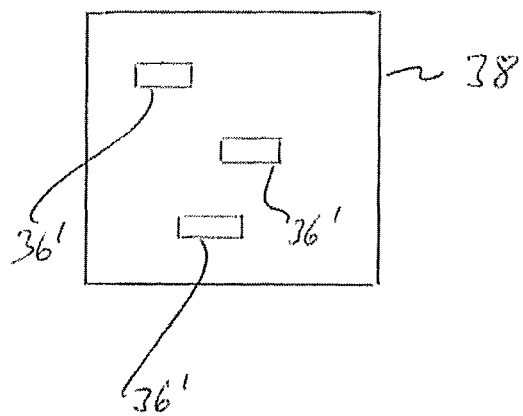

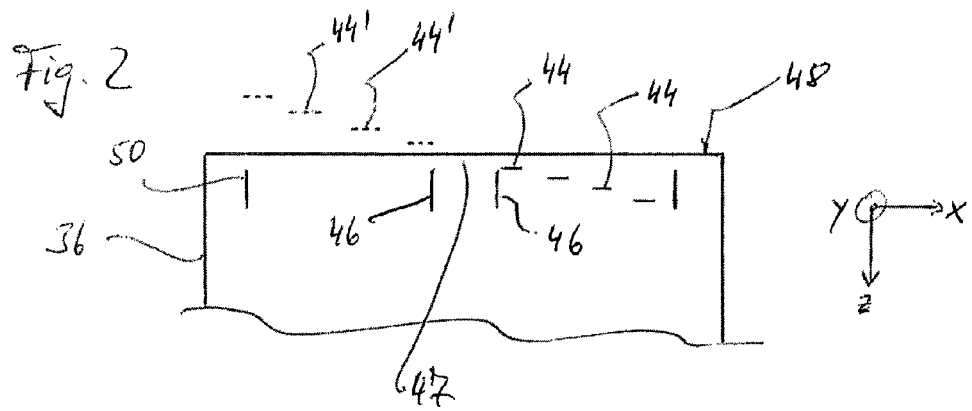
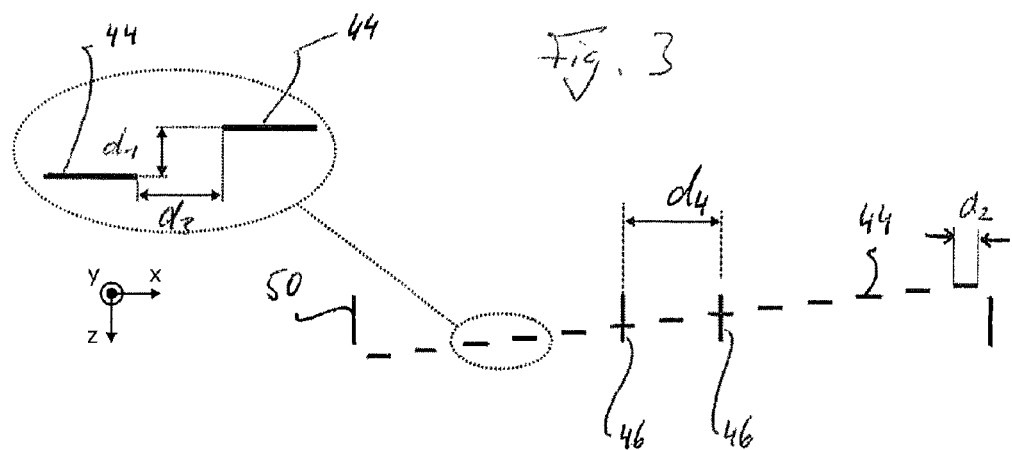
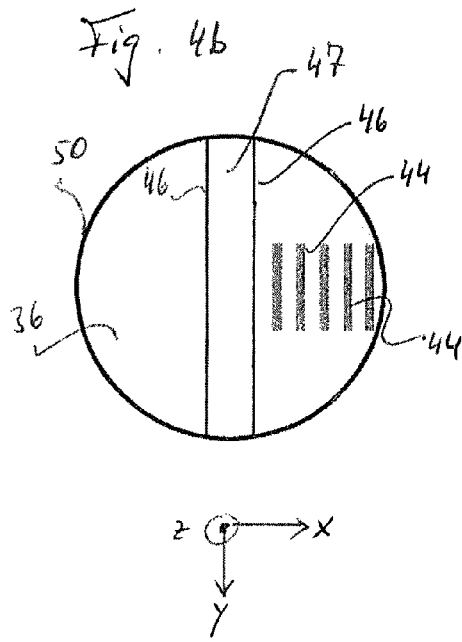
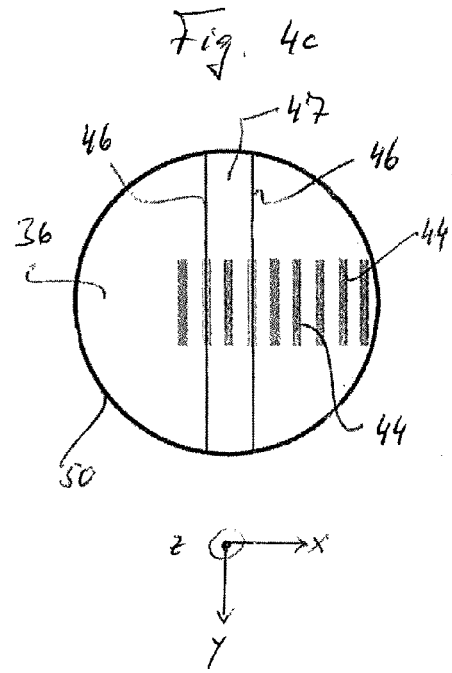

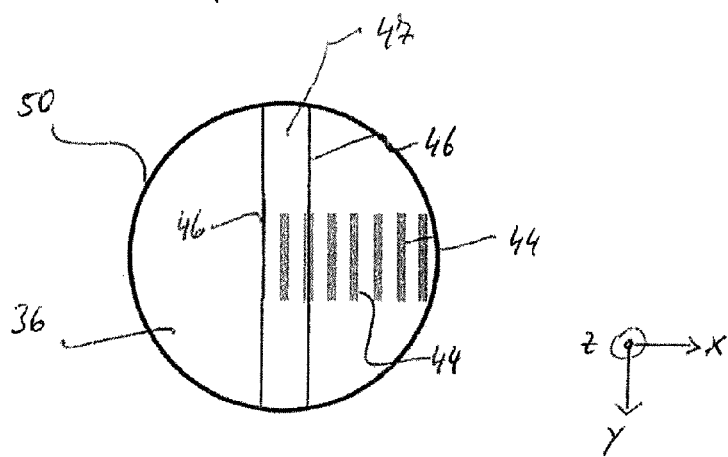
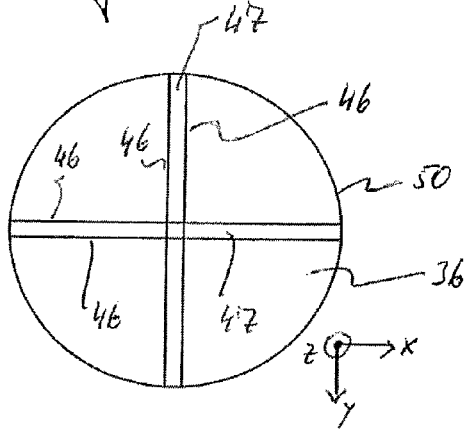
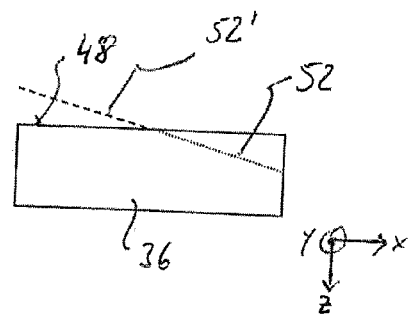
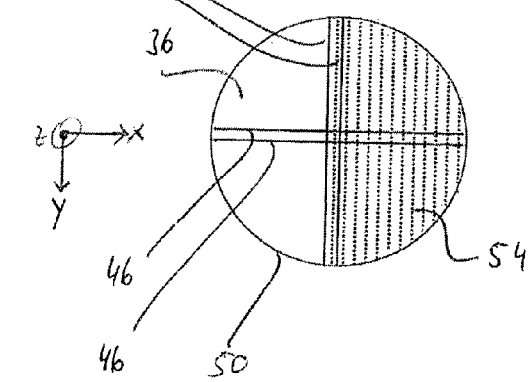
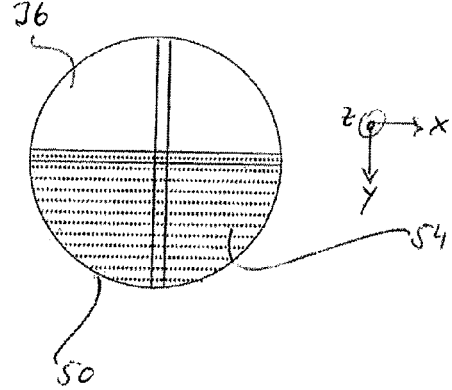

PROCESS FOR TESTING A LASER DEVICE

The invention is concerned with methods for testing a laser device that is capable of being utilised for machining an object and that has been set up to emit pulsed focused laser radiation. In particular, the methods are to enable an examination of the positioning accuracy of the radiation focus of the laser radiation.

BACKGROUND OF THE INVENTION

For the purpose of machining objects deep within the object material it is known to use ultra-short-pulse laser radiation with pulse durations within the femtosecond (fs) range (where appropriate, extending into the single-digit picosecond range), which is able to bring about a laser-induced optical breakthrough at the focus and, resulting from this, a photodisruption that is substantially restricted to the area of focus. The prerequisite for this is a transparency of the object being machined in respect of the laser radiation, which obtains, for example, in the case of machining operations on the human eye above a wavelength of about 300 nm. In the case of laser machining of the human eye, fs laser radiation is employed, in particular, for the purpose of generating incisions in the cornea or in other tissue parts of the eye, for instance within the scope of a LASIK treatment (LASIK: laser in-situ keratomileusis) for generating a flap, in the course of a corneal lenticle extraction for the purpose of generating a lenticular intracorneal lamella, or in the course of a corneal keratoplasty for the purpose of excising a piece of corneal tissue to be replaced or transplanted.

In all these forms of machining, a high positioning accuracy of the laser focus in all three spatial coordinates in the target tissue is required, in which connection currently conventional accuracy requirements stipulate a few μm and, in the best-possible case, permit positioning tolerances of only 1 μm or 2 μm.

At least the fs laser devices employed in laser surgery on the human eye often possess a mechanical interface unit, sometimes designated as a patient adapter, with a contact element that is transparent to the laser radiation and that exhibits a contact surface which has to be brought into planar abutting contact with the surface of the eye or generally with the object to be machined. The interface unit is, for example, an exchangeable module that can be coupled to focusing optics of the laser device. The contact element with its contact surface may serve as positional reference for the adjustment of the position of the radiation focus. Insofar as the eye is applied onto the contact element, a precise machining of the eye is possible, assuming a precise referencing of the focal position in relation to the contact surface.

The invention aims to make available to the user of an fs laser device a routine test that enables a simple examination of the accuracy of the positioning of the focus, in particular in the direction of propagation of the laser radiation (hereinafter called the z-direction). The test and its result are preferentially to be capable of being documented in straightforward manner.

For the purpose of examining the spatial location and orientation of the contact surface of a contact element, designed as an applanation plate, of a laser device, US 2006/0114469 A1 proposes moving the radiation focus along predetermined circular paths and registering, with a photodetector, plasma sparks which arise if the focus at the edge of the applanation plate impinges on the latter.

BRIEF SUMMARY OF THE INVENTION

In contrast, the invention provides a process for testing a laser device that has been set up to emit pulsed focused laser radiation having a focal position which is adjustable both in and across the direction of propagation of the laser radiation, the laser device including a contact element that is transparent to the laser radiation and has an abutment surface for abutment of an object to be machined, the process comprising the following steps:

applying onto the abutment surface a test object that is transparent to the laser radiation at least in a machining region, beaming the laser radiation into the test object bearing against the abutment surface and in the process moving the focal position in accordance with a predetermined test pattern for the purpose of generating enduring machining structures in the test object.

The invention furnishes the user with a simply applicable method with which it can be determined within the daily routine whether the laser device complies with the demands made of the positioning accuracy of the radiation focus. For this test a suitable test object (reference sample) is made available which, after the test has been carried out, can be preserved and archived in the long term. Because enduring machining structures are generated in the test object within the scope of the test, the test and its result can also readily be reconstructed at a later time. The test object may, for example, be disc-shaped or plate-shaped. Suitable by way of material of the test object that is transparent to the laser radiation is, for example, PMMA (polymethyl methacrylate), though other materials, in particular other transparent, non-absorbing plastic materials, are by no means ruled out.

In one embodiment of the process, the machining structures include one or more discoloration zones which contrast optically with surrounding material regions of the test object. Whenever a discoloration is mentioned here, this is not to be understood as a reference to the creation or changing of a genuine color. Since the radiant energy beamed in may result in a local photodisruption of the material of the test object, the discoloration may consist, for example, in a mere local darkening (blackening) or in the creation of a milky/dull patch. The discoloration may accordingly consist in a local change in brightness or in a change in the grey level of the material of the test object by virtue of an arbitrary modification of the material which has been triggered by the laser radiation. In any case, in this configuration the interaction of the laser radiation with the material of the test object brings about the creation of a zone that can be detected with the naked eye or/and with a camera-based image-recognition system and that stands out optically in relation to the surrounding material regions of the test object and accordingly constitutes an optical contrast with these surrounding material regions.

The machining structures preferably include at least one first discoloration structure optically contrasting with surrounding material regions of the test object, which ascends in the test object along a direction of structural extent extending across, in particular in rectilinearly oblique manner, the direction of propagation of the laser radiation (z-direction) as far as an outer surface of the test object facing towards the abutment surface. The first discoloration structure may, for example, be represented by a stripe pattern consisting of a plurality of successive discoloration stripes along the direction of structural extent. Alternatively, the first discoloration structure may be represented by a flat discoloration surface ascending obliquely in relation to the direction of propagation of the laser radiation as far as the outer surface of the test object.

In the case of the configuration of the first discoloration structure as a stripe pattern, the discoloration stripes with their stripe plane are preferentially oriented orthogonally to the direction of propagation of the radiation. Stripes following one another pairwise may in this case have a mutual separation in the direction of propagation of the radiation of at most 10 µm, better at most 8 µm, still better at most 6 µm and, for example, 5 µm. In the case of observation of a projection of the stripe pattern onto a plane that is orthogonal to the direction of propagation of the radiation, stripes following one another pairwise may have mutual separation. It is, of course, not excluded that, in the case of such a projection observation, stripes following one another pairwise are substantially free from any separation from one another.

In a preferred embodiment, the machining structures generated in the test object include a second discoloration structure optically contrasting with surrounding material regions of the test object, which forms one or more reference markings for the piercing region of the first discoloration structure through the outer surface of the test object. Depending on the location of the piercing region of the first discoloration structure relative to the reference markings, a statement is possible about the quality of the z-calibration of the laser device. Advantageously, the reference markings mark a specified piercing region of the first discoloration structure through the outer surface of the test object. Depending on whether the first discoloration structure pierces the outer surface of the test object inside or outside the specified piercing region, the test can be described as passed or not passed. Such an evaluation is particularly easy both for the user and for an automated, camera-based evaluating system. For the purpose of marking the specified piercing region, the reference markings may, for example, form a pair of marking lines running alongside one another in parallel with a separation.

The test pattern may provide for the generation of a third discoloration structure optically contrasting with surrounding material regions of the test object, which runs along the outer boundary of a predetermined available positioning field for the focal position that is orthogonal to the direction of propagation of the radiation. This available positioning field represents the maximal scan region in which the radiation focus can nominally be adjusted in a transverse plane relative to the direction of propagation of the radiation (hereinafter called the x,y plane). The boundaries of this scan region may, for example, have been defined by constructional or other structural features of the scanner used for x,y deflection of the laser radiation or/and by control-engineering presets. Frequently the maximal scan region in the x,y plane is defined by a circle. By the third discoloration structure being generated directly on the outer boundary of the nominally available maximal x,y scan region, it can easily be discerned whether the maximal scan region can actually be traversed by the scanner. For if interruptions arise in the third discoloration structure, this is an indication that in the interruption region the nominally available maximal scan region cannot actually be fully utilised.

In an alternative embodiment, the machining structures may include one or more cut surfaces by which the test object is separated into at least two partial objects detached from one another. By subsequent gauging of at least a fractional number of the partial objects, equally a statement is possible about the z-positioning accuracy of the radiation focus and hence about the z-calibration of the laser device. This gauging may, in turn, be carried out by the user himself, or it may be carried out in automated manner by means of a suitable gauging system.

According to a further embodiment, the cut surfaces may separate out from the outer surface of the test object bearing against the abutment surface a, for example, plate-shaped or disc-shaped partial object, the partial object that is separated out possessing uniform thickness or possessing several step-like regions of differing thickness which are offset from one another.

The test object is preferentially manufactured in its machining region from a material that is transparent in the visible wavelength region and at the wavelength of the laser radiation.

The test object may be formed homogeneously at least in its machining region. Alternatively, it is conceivable that the test object is of multilayer construction at least in its machining region and the interactive reaction to the laser radiation beamed in is different in different material layers of the test object.

In order to hold the test object on the contact element during the implementation of the test, suction force may be employed. For this purpose the contact element or a retaining body carrying said contact element may have been constructed with one or more suction chambers which are open towards the test object and which are capable of being evacuated by an evacuation pump.

It has already been mentioned that the test object or its parts can be enduringly preserved after the generation of the machining structures. The archiving of the machined test object (or of its parts) is expediently undertaken with assigned date or/and time data which advantageously provide an indication of the time of the implementation of the test. Accordingly, at a later time it is possible to reconstruct at any time which archived test object is associated with the test last carried out prior to an eye treatment and whether this test was successful or not.

The process may furthermore include an enabling of the laser device for a laser treatment of the human eye if a success of the test of the laser device is determined, or a disabling of the laser device for a laser treatment of the human eye if a failure of the test of the laser device is determined. This enabling or disabling can be brought about by a program-controlled control unit of the laser device, whereby a disabling of the laser device can be cancelled, for example, only by a following successful implementation of a renewed test. The determination of whether or not the test was carried out successfully can be undertaken by the control unit, for example on the basis of a user input via an input device of the laser device. For this purpose the control unit may, for example, prompt the user, by means of an appropriate prompt on a monitor, to enter his/her own assessment of the result of the test, for instance via a keyboard, a pointing device or some other form of input device. Depending on which evaluation the user enters, the control unit determines whether or not the test was successful and thereupon brings about an enabling or disabling of the laser device. In the course of the archiving of the test object, the evaluation entered by the user may also be stored.

In an alternative embodiment, the evaluation of the test result can be undertaken automatically by a suitable gauging and evaluating system.

BRIEF DESCRIPTION OF THE DRAWINGS

The invention will be elucidated further in the following on the basis of the appended drawings. Represented are:

FIG. 1: a greatly schematised block diagram of a laser machining device in the course of implementation of a calibration test according to an embodiment, FIG. 2: schematically, a test object that is used for the calibration test, with machining structures introduced therein, according to an embodiment, FIG. 3: details of the machining structures introduced into the test object shown in FIG. 2, FIGS. 4a to 4c: schematically, different test results, FIG. 5: an example of reference markings that can be introduced into a test object within the scope of a calibration test as part of the machining structures, FIG. 6: a test object with a machining structure introduced therein according to a further embodiment, FIGS. 7a and 7b: exemplary test results for a test object provided with the reference markings shown in FIG. 5, FIG. 8: a test object according to a further embodiment.

DETAILED DESCRIPTION OF PREFERRED EMBODIMENTS

Figure 8:
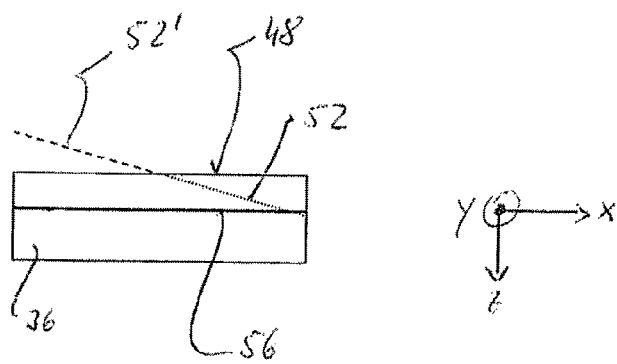

Reference will firstly be made to FIG. 1. The laser machining device shown therein—denoted generally by 10—serves for placing incisions in the human eye by means of laser technology. It will be understood that this is only an exemplary application; in principle, the laser machining device 10 may also serve for other machining purposes.

The laser machining device 10 includes a laser-source 12 which emits a pulsed laser beam 14 with pulse durations within the femtosecond range, for instance within the three-digit femtosecond range. Focusing optics 16 focus the laser beam 14 onto a focal point 18, the position of the beam focus 18 in the direction of beam propagation (z-direction) and also in a plane perpendicular thereto (x,y plane) being adjustable by means of scan components 20 which here, for the purpose of better clarity of layout, are represented as a unified functional block. The laser-source 12 and the scan components 20 are capable of being controlled by a program-controlled control unit 22, to which a monitor 24 and also an input device 26 (e.g. keyboard, pointing device, etc.) are attached.

For the purpose of positionally accurate coupling of the laser radiation into the eye to be machined, the laser machining device 10 possesses an interface unit (patient adapter) 28 which is detachably coupled to a casing of the focusing optics 16 and which exhibits a contact element 30 transparent to the laser radiation and also a holder 32 for the contact element 30. In the exemplary case shown, the contact element 30 is constructed as a plane-parallel applanation plate; however, it may be fashioned otherwise on its side facing towards the eye or/and on its side facing away from the eye; for example, it may be concave or convex. The side of the contact element 30 facing towards the eye forms an abutment surface 34 which can serve as positional reference for the eye to be treated. With a view to treating an eye, the latter is brought into abutting contact with the abutment surface 34, in which connection a suction ring, not represented in any detail, may previously be mounted onto the eye in a manner known as such, said suction ring being, in turn, capable of being firmly coupled with the interface unit 28, for example by suction force.

The abutment surface 34 of the contact element 30 constitutes a z-reference which enables a highly precise positioning of the beam focus 18 within the object to be machined. For the purpose of examining the z-calibration of the laser machining device 10, the control unit 22 has been set up to bring about the implementation of a calibration test in which by means of the laser beam 14 defined test machining structures are worked into a test object 36 applied onto the abutment surface 34, the test machining structures remaining enduringly in the test object 36 and hence enabling a permanent documentation of the result of the test. After implementation of the test, the machined test object 36 (or at least a part of the same) is saved in an archive indicated schematically at 38. FIG. 1 shows some test objects already archived in the archive 38, which for the purpose of better differentiation from the test object 36 to be machined, bearing against the abutment surface 34, are denoted by 36'.

For the purpose of generating the test machining structures, the control program (not represented in any detail) of the control unit 22 contains suitable instructions in order to move the beam focus 18 in a manner corresponding to a predetermined test scan pattern. A first configuration provides that the interaction of the laser radiation with the material of the test object 36 brings about an enduringly local discoloration in the test object 36, so that a discoloration pattern arises in the test object 36 in a manner corresponding to the test scan pattern. In the case of a test object 36 that is transparent within the visible wavelength region and to the laser radiation, the discoloration may, for example, consist in the material of the test object 36 becoming milky in the region of focus. In another configuration, the test scan pattern provides for the generation of incisions in the test object 36, in particular such incisions that result in a partitioning of the test object 36 into several partial objects. For the purpose of documenting the test, all the partial objects or only a fractional number of the partial objects may then be saved in the archive 38.

The test object 36 is, for example, a plate-like piece consisting of PMMA, which can be held on the interface unit 28 by suction force. For this purpose the interface unit 28 is equipped, in a manner not represented in any detail, with an evacuation port to which an evacuation pump 42 is capable of being attached via an evacuation line 40.

Reference will now additionally be made to FIGS. 2 and 3. These Figures represent discoloration structures that, according to an embodiment, can be introduced into the test object 36 by means of the fs laser radiation of the laser machining device 10. The discoloration structures include a stripe pattern ascending in the z-direction in stair-like manner, consisting of a plurality of discoloration stripes 44 oriented in each instance parallel to the x,y plane, and also two reference markings 46 running alongside one another in parallel along the x-y plane with a separation, which in the exemplary case shown appear as straight lines in top view of the x,y plane. Regardless of this, the two reference markings 46 may have been formed as two-dimensionally extended reference stripes or reference planes and possess a corresponding extent in the z-direction. But on account of their linear appearance in top view of the x,y plane the two reference markings 46 will be designated hereinafter as reference lines. These reference lines 46 define between themselves a specified piercing region 47 in which, given appropriate z-calibration of the laser machining device 10, the stripe pattern formed by the discoloration stripes 44 should pierce the outer surface of the test object facing towards the abutment surface 34—denoted by 48 in FIG. 2. Accordingly, the test scan pattern is designed in such a way that given appropriate z-calibration of the laser machining device 10—when observed in the direction of ascent of the stripe pattern—the last visible discoloration stripe 44 should lie within the specified piercing region 47. This situation is illustrated in FIG. 4a. FIGS. 4b and 4c illustrate, on the other hand, cases of an incorrect z-calibration of the laser machining device 10, in which the stair pattern of the discoloration stripes 44 pierces the outer surface 48 of the test object 36 in one instance ahead of the specified piercing region 47 delimited by the reference lines 46 (FIG. 4b) and in the other instance behind it (FIG. 4c). From the gradient of the stair pattern, in the cases of FIGS. 4b and 4c the necessary degree of correction for correcting the z-calibration of the laser machining device 10 can readily be ascertained, or it may be decided that the process has to be terminated.

For example, the mutual z-separation of the discoloration stripes 44—denoted in FIG. 3 by $d_1$—amounts to 5 μm. With such a value for the separation $d_1$ it can be ensured that the beam focus can be positioned and checked with an inaccuracy of at most 5 μm in the z-direction.

The stripe width—denoted in FIG. 3 by $d_2$—amounts, for example, to about 250 μm. The mutual separation of the discoloration stripes 44 in x,y projection—denoted in FIG. 3 by $d_3$—may, for example, correspond to the stripe width $d_2$, in the present case accordingly may likewise have a value of about 250 μm. The mutual separation of the reference lines 46—denoted in FIG. 3 by $d_4$—amounts, in the exemplary case shown, to four times the stripe width $d_2$. In the case of a stripe width of 250 μm, dimension $d_4$ therefore amounts to 1000 μm. Via the gradient (for example, 5 μm/500 μm), a miscalibration which possibly obtains may also be calculated.

For the purpose of generating the discoloration stripes 44 in the test object 36 the test scan pattern defines a stair pattern which consists of a plurality of stair steps corresponding to the discoloration stripes 44, whereby each stair step may be formed by several scan lines running alongside one another in the longitudinal direction of the steps. It will be understood that only those stair steps of this stair scan pattern which extend within the material of the test object 36 result in a corresponding discoloration stripe 44 in the test object 36. As a rule, a fractional number of the stair steps of the stair scan pattern will remain outside the test object 36, even in the case of a slight miscalibration of the laser machining device 10 in the z-direction. Such stair steps of the stair scan pattern lying outside the test object 36 are indicated in dashed manner in FIG. 2 at 44'.

The discoloration structures that are generated in the test object 36 include, in addition, a circular line 50 situated substantially parallel to the x,y plane, which, for example, may correspond to a maximally available x,y scan region of the laser machining device 10 or may extend within such a maximal x,y scan region with a separation from the outer boundaries thereof. For example, the circular line 50 may be generated with a diameter such as is typical of a corneal flap generated by laser technology within the scope of an fs LASIK treatment. Conventional flap diameters lie, for example, within the range between 9 mm and 11 mm. The circular line 50 may accordingly have, for example, a diameter of 10 mm or 11 mm. If said circular line can be discerned completely and in undistorted manner in the test object 36 as an annular discoloration, this is an indication that at least the scan region needed for the generation of the flap is available in unrestricted manner.

FIG. 5 shows a variant in which the discoloration pattern inscribed into the test object 36 includes two pairs of reference lines 46 at right angles to one another in x-y projection. This makes it possible to introduce into the test object 36, in two mutually perpendicular directions in each instance, a discoloration pattern ascending rectilinearly in stair-like manner or otherwise.

As an alternative to a discoloration pattern ascending in stair-like manner, FIG. 6 shows a flat discoloration surface 52 which, in the manner of viewing of FIG. 6, which represents an x,z section, appears as a straight line. The discoloration surface 52 may, for example, be realised by a plurality of lines scans of the beam focus running alongside one another in the plane of the discoloration surface 52. These line scans together form a planar scan pattern, the parts of which situated outside the test object 36 are indicated in FIG. 6 in dashed manner at 52'. In a similar manner to that in the case of the discoloration stripes 44, the calibration accuracy of the laser machining device 10 can be assessed on the basis of the position of the piercing line at which the discoloration surface 52 strikes the outer surface 48 of the test object 36 (the concept of piercing is to be understood here figuratively, since the step pattern formed by the discoloration stripes 44 and also the discoloration surface 52 do not, of course, continue outside the test object 36; for an observer looking at the outer surface 48, however, it looks as if the outer surface 48 is pierced by the stripe pattern or by the discoloration surface 52).

FIGS. 7a and 7b illustrate the case where, given a test object with two mutually perpendicular pairs of reference lines 46 (corresponding to the variant shown in FIG. 5), a flat discoloration surface similar to the representation of FIG. 6 is introduced into the test object 36, assigned to each pair of reference lines.

The scan lines traced by the beam focus for the purpose of realising the discoloration surface can be discerned. These are denoted by 54 and lie sufficiently closely together that to the observer a two-dimensional discoloration impression appears. Both in FIG. 7a and in FIG. 7b the respective discoloration surface pierces the outer surface of the test object 36 within the specified (target) piercing region defined between the pair of reference lines in question, i.e. an appropriate calibration obtains.

In the embodiment shown in FIG. 8 the test object 36 is of multilayer construction and exhibits an interlayer 56 consisting of a material differing from that in the regions of the test object 36 situated in the z-direction above and below the interlayer 56. The material of the interlayer 56 displays a different interactive reaction with the laser radiation beamed in within the scope of the calibration test from that of the remaining material regions of the test object 36. For example, the interaction of the laser radiation with the material of the interlayer 56 results in a discoloration that is different from that in the remaining material regions of the test object 36. With given z-separation of the interlayer 56 from the outer surface 48 of the test object 36, with the aid of the mutual separation of the points of piercing of the discoloration surface 52 through the outer surface 48 and the interlayer 56 not only can the z-calibration be examined for a possible z-offset but an examination for correct scaling of the z-axis of the coordinate system used by the laser machining device 10 can also be performed. For the purpose of unambiguous determination of the point of piercing of the discoloration surface 52 through the interlayer 56, it may be advantageous to construct the test object 36 with a polished, preferentially rectilinear lateral surface, so that both the discoloration surface 52 and the interlayer 56 are discernible in a lateral observation. For this purpose the test object 36 may be constructed, for example, as a half-disc or quarter-disc.

Figure 9:
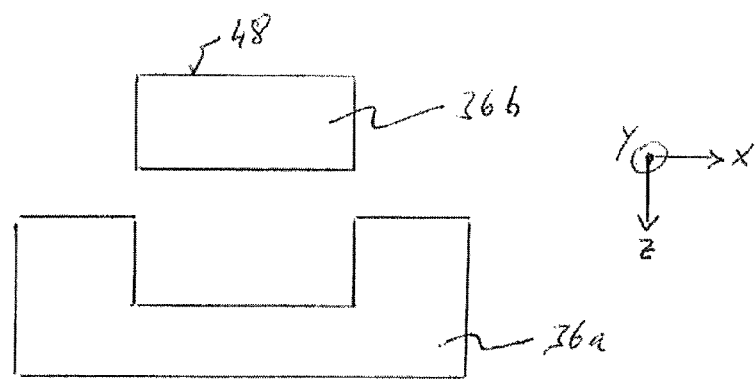
FIG. 9: schematically, an example of a partitioning of a test object into partial objects within the scope of a calibration test
Figure 10:
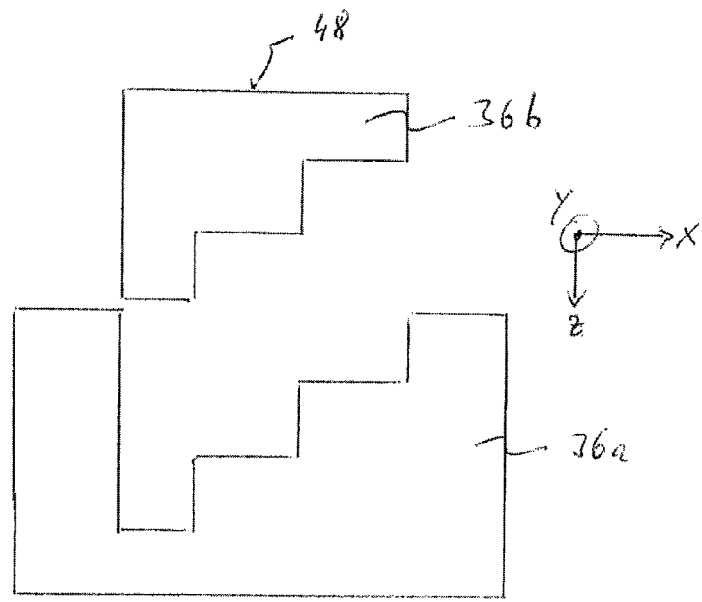
FIG. 10: a further example of a partitioned test object.

FIGS. 9 and 10 show, in a manner not true to scale, two embodiments in which the machining structures introduced into the test object 36 constitute incisions which result in a separation of the test object 36 into partial objects 36a, 36b. For example, a plate-like partial object (FIG. 9) or a partial object stepped in stair-like manner (FIG. 10) can be cut out of the outer surface 48 of the test object. By a thickness measurement of the excised partial object 36b in the z-direction, inferences as to the accuracy of the z-calibration of the laser machining device 10 can subsequently be obtained. The thickness measurement may, for example, be carried out with optical, acoustic or mechanical measuring means. As an alternative to a gauging of partial object 36b, it is conceivable to gauge the z-depth of the surface depression that has arisen in the remaining partial object 36a as a consequence of taking out partial object 36b.

After placement of the machining structures in the test object 36, the control unit 22 of the laser machining device 10 can bring about the output of a prompt on the monitor 24 which prompts the user to enter, via the input device 26, whether the calibration test was successful or not. Depending on the input of the user, the control unit 22 then brings about an enabling or disabling of the laser machining device 10 for later eye operations.

In a preferred embodiment, suitable precautions may have been provided in order to aspirate vapour or/and particles which may arise in the course of generating the machining structures in the test object.

The invention claimed is:

1. A process for testing a laser device adapted to emit pulsed focused laser radiation having a focal position which is adjustable both in and across a direction of propagation of the laser radiation, the laser device including a contact element that is transparent to the laser radiation and has an abutment surface for abutment of an object to be machined, the process comprising the following steps:
   applying onto the abutment surface a test object that is transparent to the laser radiation at least in a machining region, the test object comprising:
      an interlayer that can yield a plurality of discoloration zones in response to the laser radiation; and
      one or more reference markings marking a specified piercing region indicating where a particular discoloration zone corresponding to a particular depth appears only if the laser device is calibrated;
   beaming the laser radiation into the test object bearing against the abutment surface and moving the focal position in accordance with a predetermined test pattern to generate permanent machining structures in the test object, the test pattern comprising instructions to move the focal position to a sequence of z-depths including the particular z-depth, the focal position generating the machining structures comprising the discoloration zones ascending in a stair-like manner in the direction of propagation of the laser radiation towards an outer surface of the test object facing the abutment surface; and
   determining a z-calibration of the laser-device by:
      if the particular discoloration zone corresponding to the particular depth appears at the specified piercing region, determining that the laser-device is calibrated; and
      if otherwise, determining a correction for correcting the z-calibration from a gradient of the stair pattern.

2. A process according to claim 1, wherein the discoloration zones contrast optically with surrounding material regions of the test object.

3. A process according to claim 1, wherein the discoloration zones comprise a plurality of discoloration stripes.

4. A process according to claim 3, wherein a stripe plane of the discoloration stripes is oriented orthogonally to the direction of propagation of the laser radiation.

5. A process according to claim 3, wherein adjacent discoloration stripes have a mutual separation in the direction of propagation of the laser radiation of at most 10 µm.

6. A process according to claim 3, wherein adjacent discoloration stripes have mutual separation when projected onto a plane that is orthogonal to the direction of propagation of the radiation.

7. A process according to claim 1, wherein the reference markings form a pair of marking lines running alongside one another in parallel with a separation to mark the target piercing region.

8. A process according to claim 1, wherein the test pattern provides for the generation of a discoloration structure that marks an outer boundary of a predetermined available positioning field for the focal position, the discoloration structure being orthogonal to the direction of propagation of the radiation.

9. A process according to claim 1, wherein the machining structures include one or more cut surfaces to separate the test object into at least two partial objects detached from one another.

10. A process according to claim 9, wherein the cut surfaces separate a partial object out of the outer surface of the test object bearing against the abutment surface, the partial object possessing uniform thickness or possessing one or more regions of differing thickness which are offset from one another in stepped manner.

11. A process according to claim 1, wherein the test object is made at least in its machining region from a material that is transparent in the visible wavelength region.

12. A process according to claim 1, wherein the test object is of multilayer construction at least in its machining region and an interactive reaction to the laser radiation beamed in is different in different material layers of the test object.

13. A process according to claim 1, wherein the test object is held onto the contact element by suction force.

14. A process according to claim 1, further including the archiving of the machined test object with at least one of an assigned date and time data.

15. A process according to claim 1, further including:
   enabling the laser device for a laser treatment of the human eye if a success of the test of the laser device is determined,
   disabling the laser device for a laser treatment of the human eye if a failure of the test of the laser device is determined.

16. A process according to claim 15, further including:
   determining the success or failure of the test on the basis of a user input via an input device of the laser device.

* * * * *